United States Patent [19]

Schmidt et al.

[11] 4,211,872

[45] Jul. 8, 1980

[54] SUBSTITUTED FUROPYRIDINONES AND FUROPYRAZINONES

[76] Inventors: Paul J. Schmidt, 3590 Concerto Dr., Sharonville, Ohio 45241; William M. Hung, 9176 Millcliff Dr., Cincinnati, Ohio 45231

[21] Appl. No.: 968,082

[22] Filed: Dec. 11, 1978

[51] Int. Cl.² .......................................... C07D 491/04
[52] U.S. Cl. .................................. 546/116; 282/27.5; 427/151; 544/350; 544/405; 544/406; 546/273; 546/315; 546/322
[58] Field of Search ....................... 546/116; 544/350; 427/151; 282/27.5

[56] References Cited

U.S. PATENT DOCUMENTS 3,509,173  4/1970  Lin .................................. 260/326.14
3,775,424  11/1973  Farber .................................. 546/116

FOREIGN PATENT DOCUMENTS 812406  7/1974  Belgium .
862217  6/1978  Belgium .
49-118515  11/1974  Japan ..................................... 282/27.5

Primary Examiner—Alan L. Rotman
Assistant Examiner—Richard A. Schwartz

[57] ABSTRACT

Substituted furopyridinones and furopyrazinones which are useful as color formers in pressure-sensitive carbonless duplicating systems and thermal marking systems are prepared by reacting diphenylamines with substituted benzoyl (or 3-indolylcarbonyl)pyridinecarboxylic acids and substituted benzoyl (or 3-indolylcarbonyl)pyrazinecarboxylic acids, respectively.

26 Claims, No Drawings

SUBSTITUTED FUROPYRIDINONES AND FUROPYRAZINONES

BACKGROUND OF THE INVENTION

1. Field of the Invention

This invention relates to a group of compounds classified in the field of organic chemistry as furopyridinones and furopyazinones useful as color formers in pressure-sensitive carbonless duplicating systems and thermal marking systems, to processes for the preparation thereof and to pressure-sensitive duplicating systems and thermal marking systems containing the same.

2. Description of the Prior Art

Several classes of organic compounds of widely diverse structural types are known to be useful as color formers for carbonless duplicating systems. Among the more widely recognized classes are phenothiazines, for example, benzoyl leuco methylene blue; fluorans, for example, 2'-anilino-6'-diethylaminofluoran; phthalides, for example, crystal violet lactone, and various other types of color formers currently employed in commercially acceptable carbonless duplicating systems. Typical of the many such systems taught in the prior art are those described in U.S. Pat. Nos. 2,712,507, 2,800,457 and 3,041,289 which issued July 5, 1955, July 23, 1957 and June 26, 1962, respectively. Many of the color formers in the prior art, however, suffer one or more disadvantages such as low tinctorial strength, poor light stability, low resistance to sublimation and low solubility in common organic solvents.

The following appears to constitute the most pertinent prior art relative to the present invention.

U.S. Pat. No. 3,775,424, issued Nov. 27, 1973, discloses in most pertinent part a series of compounds reportedly employed in pressure-sensitive record material and mark-forming mainfold systems and having the formula

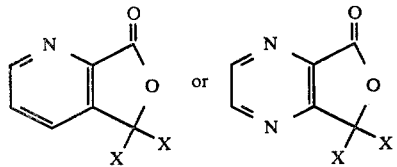

wherein inter alia each X is

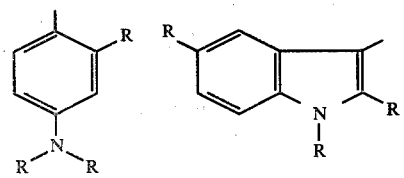

and each R is hydrogen, an alkyl radical having 1 to 4 carbon atoms, an alkoxy radical having 1 to 4 carbon atoms or a phenyl radical.

Belgian Pat. No. 812,406 published July 1, 1974 discloses in most pertinent part a pressure-sensitive copying paper containing as a color former a compound having the formula

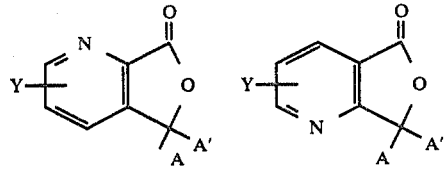

or a mixture thereof wherein inter alia Y is hydrogen and one of A and A' is indolyl and the other is a nitrogen or sulfur containing heterocyclic group.

3. Prior Publications

Belgian Pat. No. 862,217, published June 22, 1978, which corresponds essentially to pending U.S. patent applications Ser. Nos. 821,926 and 942,996, filed Aug. 4, 1977 and Sept. 18, 1978, respectively, in the names of Paul Joseph Schmidt and William Mo-Wei Hung, the inventors in the instant application, discloses a series of phthalides useful as color formers in pressure-sensitive carbonless duplicating systems, thermal marking systems and hectographic or spirit-reproducing copying systems and having the formula

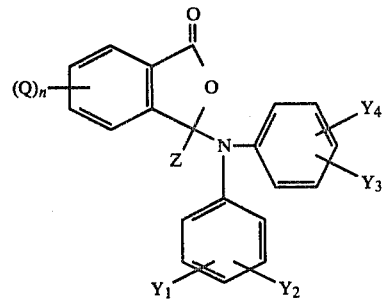

wherein:

Q is di-lower-alkylamino, nitro, halo or COX, where X is hydroxyl, benzyloxy, alkoxy having from 1 to 18 carbon atoms or OM where M is an alkali metal cation, an ammonium cation or a mono-, di- or tri-alkylammonium cation having from 1 to 18 carbon atoms;

n is 0; or 1 when Q is di-lower-alkylamino, nitro or COX; or from 1 to 4 when Q is halo;

$Y_1$, $Y_2$, $Y_3$ and $Y_4$ are the same or different and are hydrogen, halo, hydroxyl, lower-alkoxy, alkyl having from 1 to 9 carbon atoms, phenyl-lower-alkyl, COOR$_4$ or NR$_5$R$_6$, where R$_4$ and R$_5$ are hydrogen or lower-alkyl and R$_6$ is hydrogen, lower-alkyl, cycloalkyl having from 5 to 7 carbon atoms or lower alkanoyl; Z is and 9-julolidinyl in which:
R is hydrogen or non-tertiary alkyl having from 1 to 4 carbon atoms;
$R_1$ is hydrogen, or non-tertiary alkyl having from 1 to 18 carbon atoms;
$R_2$ is hydrogen, phenyl or non-tertiary alkyl having from 1 to 4 carbon atoms;
$R_3$ is hydrogen, non-tertiary alkyl having from 1 to 4 carbon atoms or non-tertiary alkoxy having from 1 to 4 carbon atoms;
$R_7$ is hydrogen, halo, lower-alkyl, lower-alkoxy or dilower-alkylamino;
$R_8$ is lower-alkyl; and
$R_9$ is lower-alkyl, benzyl, phenyl or phenyl substituted with a lower-alkyl or lower-alkoxy group.

SUMMARY OF THE INVENTION

The present invention provides novel furopyridinones and furopyrazinones useful as color formers in pressure-sensitive duplicating systems and thermal marking systems. The compounds develop colored images of good to excellent tinctorial strength; possess high resistance to sublimation, enhanced solubility in common organic solvents and have the particular advantage of excellent light stability.

In a composition-of-matter aspect the invention relates to a series of 7-(and 5-)(2-$R_3$-4-$NR_4R_5$-phenyl) or (1-$R_6$-2-$R_7$-3-indolyl)-7-(and 5-)[($Y_1$-$Y_2$-phenyl)($Y_3$-$Y_4$-phenyl)amino]furo[3,4-b]pyridine-5(7H)-[and 7(5H)-]ones, 3-(and 1-)(2-$R_3$-4-$NR_4R_5$-phenyl) or (1-$R_6$-2-$R_7$-3-indolyl)-3-(and 1-)[($Y_1$-$Y_2$-phenyl)($Y_3$-$Y_4$-phenyl)amino]furo[3,4-c]pyridine-1(3H)-[and 3(1H)-]-ones and 7-(2-$R_3$-4-$NR_4R_5$-phenyl)or (1-$R_6$-2-$R_7$-3-indolyl)-7-[($Y_1$-$Y_2$-phenyl)($Y_3$-$Y_4$-phenyl)amino]furo[3,4-b]pyrazine-5(7H)ones which are useful as color formers in pressure-sensitive carbonless duplicating systems and thermal marking systems.

In a process aspect the present invention provides a process for preparing 7-(and 5-)(2-$R_3$-4-$NR_4R_5$-phenyl) or (1-$R_6$-2-$R_7$-3-indolyl)-7-(and 5-)[($Y_1$-$Y_2$-phenyl)($Y_3$-$Y_4$-phenyl)amino]furo[3,4-b]pyridine-5(7H)-[and 7(5H)-]ones, 3-(and 1-)(2-$R_3$-4-$NR_4R_5$-phenyl) or (1-$R_6$-2-$R_7$-3-indolyl)-3-(and 1-)[($Y_1$-$Y_2$-phenyl)-($Y_3$-$Y_4$-phenyl)amino]furo[3,4-c]pyridine-1(3H)-[and 3(1H)-]ones and 7-(2-$R_3$-4-$NR_4R_5$-phenyl) or (1-$R_6$-2-$R_7$-3-indolyl)-7-[($Y_1$-$Y_2$-phenyl)($Y_3$-$Y_4$-phenyl)amino]furo[3,4-b]pyrazine-5(7H)-ones which comprises reacting a ($Y_1$-$Y_2$-phenyl)($Y_3$-$Y_4$-phenyl)amine with a 2-(and 3-)(2-$R_3$-4-$NR_4R_5$-benzoyl) or (1-$R_6$-2-$R_7$-3-indolylcarbonyl)-3-(and 2-)pyridinecarboxylic acid, a 3-(and 4-)(2-$R_3$-4-$NR_4R_5$-benzoyl) or (1-$R_6$-2-$R_7$-3-indolylcarbonyl)-4-(and 3-)-pyridinecarboxylic acid or a 3-(2-$R_3$-4-$NR_4R_5$-benzoyl) or (1-$R_6$-2-$R_7$-3-indolylcarbonyl)-2-pyrazinecarboxylic acid, respectively.

This invention further provides a second process for preparing the above-named furopyridinones and furopyrazinones which comprises reacting the appropriate above-named pyridinecarboxylic acid or pyrazinecarboxylic acid with an inorganic acid chloride followed by reaction of the product so-obtained with a ($Y_1$-$Y_2$-phenyl)($Y_3$-$Y_4$-phenyl)amine.

In an article-of-manufacture aspect the present invention relates to a pressure-sensitive carbonless duplicating system or thermal marking system containing a color forming substance comprising at least one of the furopyridinones or furopyrazinones of the invention.

DETAILED DESCRIPTION OF THE INVENTION INCLUSIVE OF THE PREFERRED EMBODIMENTS

This invention in a composition-of-matter aspect resides in a compound having Formula I:

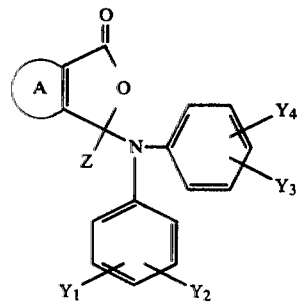

wherein A is

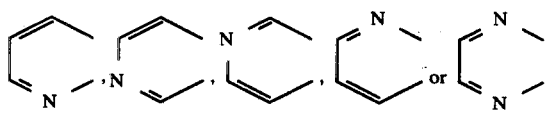

$Y_1$, $Y_2$, $Y_3$ and $Y_4$ are the same or different and are selected from the group consisting of hydrogen, halo, lower alkoxy, alkyl having from 1 to 9 carbon atoms, phenyl-lower-alkyl and $NR_1R_2$ where $R_1$ is hydrogen or lower alkyl and $R_2$ is hydrogen, lower alkyl, lower alkanoyl, phenylsulfonyl or loweralkyl-substituted phenylsulfonyl;

Z is

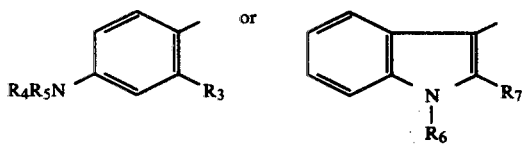

in which
$R_3$ is hydrogen, lower alkyl, lower alkoxy, halo or di-lower-alkylamino;
$R_4$ is lower alkyl;
$R_5$ is lower alkyl or benzyl;
$R_6$ is hydrogen or non-tertiary alkyl having from 1 to 18 carbon atoms; and
$R_7$ is hydrogen, phenyl or non-tertiary lower alkyl.

The compounds are useful as color formers in pressuresensitive carbonless duplicating systems and thermal marking systems.

A particular embodiment sought to be patented resides in a compound having Formula I hereinabove wherein $Y_1$, $Y_2$, $Y_3$ and $Y_4$ have the previously given meanings; A is

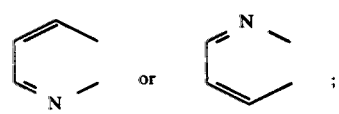

and Z is

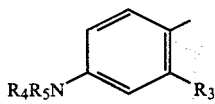

$R_3$, $R_4$ and $R_5$ having the previously given meanings. Preferred compounds within the ambit of this particular embodiment are 7-[4-(dimethylamino)phenyl]-7-(diphenylamino)furo-[3,4-b]pyridine-5(7H)-one 5-[4-(dimethylamino)phenyl]-5-(diphenylamino)furo-[3,4-b]pyridine-7(5H)-one 7-[4-(dimethylamino)phenyl]-7-[bis(4-octylphenyl)amino]furo[3,4-b]pyridine-5(7H)-one 5-[4-(dimethylamino)phenyl]-5-[bis(4-octylphenyl)amino]furo[3,4-b]pyridine-7(5H)-one 7-[4-(diethylamino)-2-methylphenyl]-7-[bis(4-octylphenyl)amino]furo[3,4-b]pyridine-5(7H)-one 5-[4-(diethylamino)-2-methylphenyl]-5-[bis(4-octylphenyl)amino]furo[3,4-b]pyridine-7(5H)-one 7-(1-ethyl-2-methyl-3-indolyl)-7-(diphenylamino)-furo[3,4-b]pyridine-5(7H)-one 5-(1-ethyl-2-methyl-3-indolyl)-5-(diphenylamino)-furo[3,4-b]pyridine-7(5H)-one 7-(1-ethyl-2-methyl-3-indolyl)-7-[bis(4-octylphenyl)amino]furo[3,4-b]pyridine-5(7H)-one and 5-(1-ethyl-2-methyl-3-indolyl)-5-[bis(4-octylphenyl)amino]furo[3,4-b]pyridine-7(5H)-one.

In one of its process aspects the invention sought to be patented resides in a process for preparing the compounds of Formula I hereinabove which comprises reacting a pyridinecarboxylic acid having Formula II

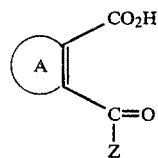

Formula II with a diarylamine having Formula III

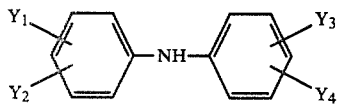

Formula III in the presence of an anhydride of an alkanoic acid having from 2 to 5 carbon atoms where in Formulas II and III, A, Z, $Y_1$, $Y_2$, $Y_3$ and $Y_4$ have the previously given meanings.

In another process aspect, the invention sought to be patented resides in the process for producing the compounds of Formula I which comprises reacting a pyridinecarboxylic acid of Formula II with an inorganic acid chloride selected from the group consisting of thionyl chloride, phosphorus oxychloride, phosphorus trichloride and phosphorus pentachloride followed by reaction of the resulting product with a diarylamine of Formula III in the presence of an organic base where in Formulas II and III, A, Z, $Y_1$, $Y_2$, $Y_3$ and $Y_4$ have the previously given meanings.

In an article-of-manufacture aspect the invention sought to be patented resides in a pressure-sensitive carbonless duplicating system or thermal marking system containing a colorforming substance comprising a compound having Formula I hereinabove.

A particular embodiment sought to be patented resides in a pressure-sensitive transfer sheet adapted for use with a receiving sheet having an electron accepting layer comprising a support sheet coated on one side with a layer of pressure-rupturable microcapsules, said microcapsules containing a liquid solution of a colorforming substance comprising at least one compound having Formula I.

Another particular embodiment sought to be patented resides in a heat-responsive record material comprising a support sheet coated on one side with a layer containing a mixture comprising at least one color-forming compound having Formula I and an acidic developer arranged such that application of heat will produce a mark-forming reaction between the color-forming compound and the acidic developer.

Preferred articles within the ambit of the particular embodiments above-described are those wherein the color-forming component comprises a compound having Formula I, especially
where
A is

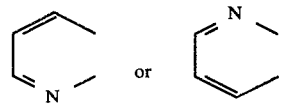

and
Z is

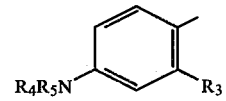

As used herein the term "halo" includes chloro, fluoro, bromo and iodo. Chloro is the preferred halo substituent because of the relatively low cost and ease of preparation of the required chloro-substituted intermediates and because the other halogens offer no particular advantages over chloro. However, the other above-named halo substituents are also satisfactory. The terms "lower-alkyl", "lower-alkoxy" and "di-loweralkylamino" denote saturated acyclic groups having from 1 to 4 carbon atoms which may be straight or branched as exemplified by methyl, ethyl, propyl, isopropyl, butyl, sec-butyl, isobutyl, tert-butyl, methoxy, ethoxy, propoxy, isopropoxy, butoxy, sec-butoxy, isobutyoxy, tert-butoxy, dimethylamino, diethylamino, ethylmethylamino, dipropylamino, dibutylamino, isobutylmethylamino, di-tert-butylamino and the like.

The term "lower-alkanoyl" denotes saturated acyclic acyl groups having from 1 to 5 carbon atoms which may be straight or branched as exemplified by formyl, acetyl, propionyl, butyryl, isobutytyl, valeryl, 2-methylbutyryl, isovaleryl, pivalyl and the like.

The term "phenyl-lower-alkyl" includes benzyl, 2-phenylethyl, 2-phenylpropyl, 3-phenylpropyl, 1-phenylbutyl, 2,2-dimethyl-2-phenylethyl and the like. If desired, the phenyl group may contain a lower alkyl or lower alkoxy substituent.

As used herein, the term "alkyl having from 1 to 9 carbon atoms" denotes saturated monovalent straight or branched chain aliphatic hydrocarbon radicals including methyl, ethyl, propyl, isopropyl, butyl, isobutyl, tert-butyl, amyl, 1-methylbutyl, 3-methylbutyl, hexyl, isohexyl, heptyl, isoheptyl, octyl, isooctyl, 2-ethylhexyl, nonyl, 3-ethylheptyl and the like.

The term "non-tert-alkyl having from 1 to 18 carbon atoms" includes in addition to the above-named alkyl groups having from 1 to 9 carbon atoms, excluding, of course, any tertiary alkyl groups, saturated monovalent straight or branched chain aliphatic hydrocarbon radicals such as n-decyl, n-undecyl, n-tridecyl, n-dodecyl, n-tetradecyl, n-pentadecyl, n-hexadecyl, n-heptadecyl, n-octadecyl, 1,3,5-trimethylhexyl, 1,5-dimethyl-4-ethylhexyl, 5-methyl-2-butylhexyl, 2-propylnonyl, 2-butyloctyl, 2-pentylnonyl, 1,2-dimethyltetradecyl and the like.

Anhydrides of alkanoic acids of 2 to 5 carbon atoms include acetic anhydride, propionic anhydride, butyric anhydride, isobutyric anhydride, valeric anhydride, isovaleric anhydride, α-methylbutyric anhydride, pivalic anhydride and the like.

Acetic anhydride is preferred because of its low cost and high reactivity. However, the other above-named anhydrides are also satisfactory.

In accordance with one of the process aspects of this invention the compounds having Formula I are obtained by reacting approximately equimolar amounts of a pyridinecarboxylic acid of Formula II and a diarylamine of Formula III in the anhydride of an alkanoic acid having from 2 to 5 carbon atoms such as acetic anhydride with or without an inert diluent at a temperature of about 0° C. to 100° C. for approximately 10 minutes to 72 hours. The reaction is usually carried out in the absence of an inert diluent at about 20°-50° C. for approximately 0.5 to 2 hours. The product thus obtained can be isolated by filtration if it is insoluble in the reaction medium or by dilution of the reaction medium with a miscible solvent in which the product is insoluble such as a lower alkanol or low molecular weight hydrocarbon, for example, isopropyl alcohol or hexane, or a mixture of these in order to effect precipitation of the product. Alternatively, the reaction mixture can be poured into aqueous base such as dilute ammonium hydroxide, sodium hydroxide, sodium carbonate or sodium bicarbonate and the product extracted with an organic solvent such as benzene or toluene followed by evaporation of the organic solvent leaving the product as a residue. The product once isolated, can be purified by conventional means such as trituration or recrystallization from a suitable solvent.

In the above reaction the diarylamine of Formula III serves as a basic catalyst. However, if desired an additional organic base such as pyridine, collidine, tri-lower-alkylamines, urea and the like can be employed. Ordinarily pyridine and urea are preferred.

In accordance with the second process aspect of the invention, a compound of Formula I can be prepared in two steps which comprise, first, reacting a pyridine carboxylic acid of Formula II with an excess of an inorganic acid chloride such as thionyl chloride, phosphorus oxychloride, phosphorus trichloride or phosphorus pentachloride with or without an inert diluent such as benzene, toluene, chloroform, 1,2-dichloroethane or N,N-dimethylformamide at 20°-80° C. for about 0.5 to 2 hours, followed by a reaction by the resulting product which, while not having been isolated, is presumed to be a chloride having Formula IV

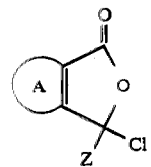

Formula IV in which A and Z have the previously given meanings, with a diarylamine of Formula III hereinabove in an inert solvent in the presence of an organic base such as pyridine, collidine, tri-lower-alkylamines or urea at a temperature in the range of 0°-80° C. for about 1 to 48 hours. The product can be isolated and purified in conventional fashion.

The pyridinecarboxylic acids and pyrazinecarboxylic acids of Formula II hereinabove which are required as starting materials in the preparation of the final products of Formula I are generally known, for example, as disclosed in U.S. Pat. No. 3,936,564, issued Feb. 3, 1976, U.S. Pat. No. 3,775,424, issued Nov. 27, 1973, Japanese Pat. No. 73/8727, published Mar. 17, 1973, Japanese Pat. No. 73/3205, published Jan. 30, 1973 and Japanese Pat. 73/8729, published Mar. 17, 1973. Those pyridinecarboxylic acids and pyrazinecarboxylic acids which are novel can be prepared in accordance with the procedures described for the preparation of the known compounds, i.e. by reacting an anhydride having Formula V

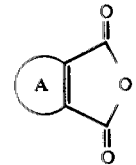

Formula V with an appropriate aniline of Formula VI or an indole of Formula VII:

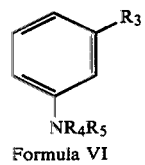 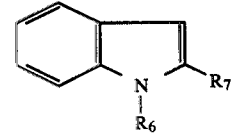

Formula VI  Formula VII wherein A, $R_3$, $R_4$, $R_5$, $R_6$ and $R_7$ in the above formulas have the previously given meanings, in the presence of a Lewis acid, for example, aluminum chloride or zinc chloride, and with a diluent such as benzene, chlorobenzene or o-dichlorobenzene at a temperature of about 0°-100° C. The reaction is conveniently carried out in benzene in the presence of aluminum chloride at about 0°-25° C. The more reactive indoles (Formula VII) can be reacted with the anhydrides (Formula V) in the absence of a Lewis acid by simply heating the reactants together in an inert solvent at about 80°-150° C.

It will, of course, be appreciated that reaction of the inherently unsymetrical anhydrides of Formula V wherein
A is

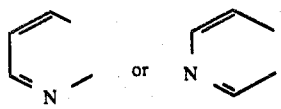 or with an aniline of Formula VI or an indole of Formula VII can produce isomers or a mixture of isomers of Z-CO-pyridinecarboxylic acids (Formula II). For example, reaction of 2,3-pyridinedicarboxylic anhydride (Formula Va hereinbelow) with an aniline or an indole of Formula VI or VII respectively (Z—H hereinbelow) can produce either a 2-(Z—CO)-3-pyridinecarboxylic acid (Formula IIa) or a 3-(Z—CO)-2-pyridinecarboxylic acid (Formula IIb) or a mixture of these. It will, of course, be appreciated that the ratio of isomers obtained will depend on various reaction conditions such as temperature, solvent, catalyst and the relative solubility of the isomers in the reaction medium. Ordinarily, when carried out as described herein the reaction produces a mixture of isomers with the 2-(Z—CO)-3-pyridinecarboxylic acid (Formula IIa) predominating in the isolated product. If desired, the mixture of isomeric Z—CO—pyridinecarboxylic acids can be separated by conventional means such as selective precipitation at different pH, fractional crystallization or chromatography and each of the individual isomers IIa and IIb can then be reacted with an appropriate diarylamine of Formula III to produce a furo-[3,4-b]pyridine-5(7H)-one of Formula Ia and a furo[3,4-b]pyridine-7(5H)-one of Formula Ib, respectively. It is generally preferred however, to simply react the isolated mixture of isomeric Z—CO-pyridinecarboxylic acids of Formulas IIa and IIb with a diarylamine to produce an isomer mixture of furopyridinones of Formulas Ia and Ib which can be separated by conventional means if desired. However, since both isomers are useful as color formers it is economically advantageous to simply use the isolated mixture thereof in the practice of this invention.

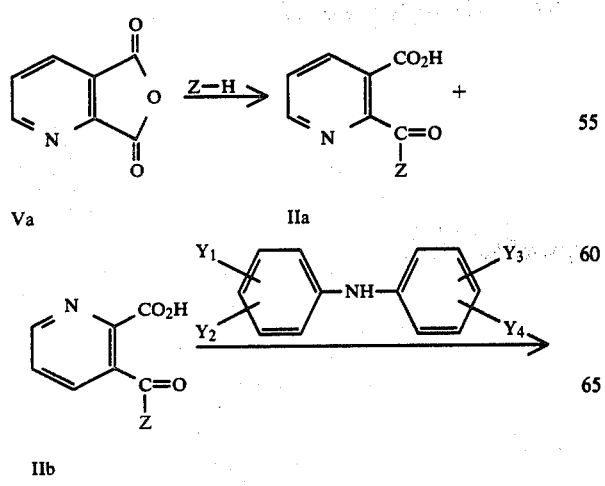

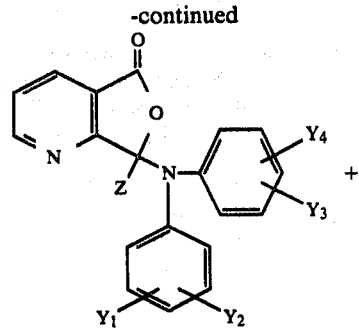

Ia

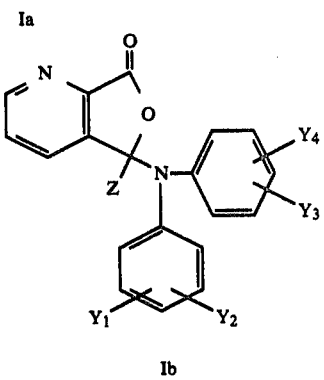

Ib

In general, it has been found that the reaction of 2,3-pyridinedicarboxylic anhydride with an indole of Formula VII in the manner described herein produces a mixture of isomers of Formulas IIa and IIb (Z is

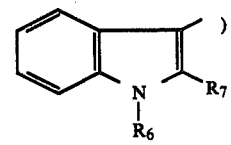

in which isomer IIa predominates in the isolated product by a factor greater than about 7. Moreover, it has been further observed that the more abundant isomer (i.e. IIa) is also the more reactive. Accordingly, subsequent reaction of the isomeric mixture of IIa and IIb with a diarylamine of Formula III produces almost exclusively furo[3,4-b]pyridine-5(7H)-one (Formula Ia) with isomer Ib being observed only in trace amounts.

The reaction of 2,3-pyridinedicarboxylic anhydride with an aniline of Formula VI in accordance with the procedures described herein also produces a mixture of isomers of Formulas IIa and IIb (Z is

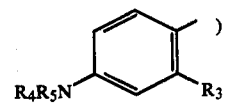

and although isomer IIa again predominates in the isolated product, significant amounts of isomer IIb are also obtained. Thus, although isomer IIa is more reactive, a sufficient concentration of the less reactive IIb is present in the mixture to afford upon reaction with a diarylamine of Formula III a mixture of isomeric furo[3,4-b]pyridinones of Formulas Ia and Ib in which isomer Ia is predominant and isomer Ib is present in minor, but significant amounts.

In like fashion, reaction of 3,4-pyridinedicarboxylic anhydride (Formula Vb hereinbelow) with an aniline of Formula VI or an indole of Formula VII (Z—H hereinbelow) produces a mixture of 3-(Z—CO)-4-pyridinecarboxylic acid (Formula IIc) and 4-(Z—CO)-3-pyridinecarboxylic acid (Formula IId). The mixture is in turn reacted with a diarylamine of Formula III to produce an isomeric mixture of furo[3,4-c]pyridine-1(3H)-one (Formula Ic) and furo[3,4-c]pyridine-3(1H)-one (Formula Id).

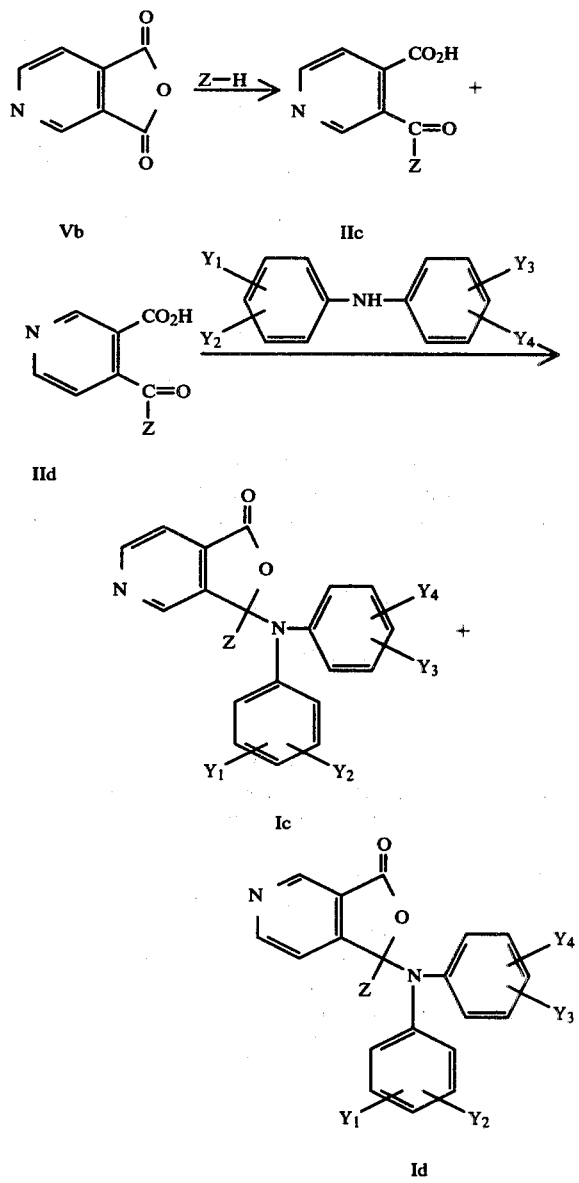

The diarylamines of Formula III which are also required as starting materials in the processes of the invention, belong to a well-known class of compounds and are either commercially available or readily obtained by conventional procedures well known in the art.

The novel compounds of Formula I hereinabove are essentially colorless in the depicted form. When contacted with an acidic medium, for example, silica gel, or one of the types ordinarily employed in pressure-sensitive carbonless duplicating systems such as silton clay or phenolic resins, the compounds of Formula I develop a yellow to black colored image of good to excellent tinctorial strength and possessing resistance to sublimation, xerographic copiability and especially excellent light stability. The compounds are thus highly suitable for use as colorless precursors, that is, color-forming substances in pressure-sensitive carbonless duplicating systems. Compounds which produce a yellow to red color can be used as toners in admixture with other color formers to produce images of a neutral shade which desirably are readily copiable by xerographic means. The compounds of Formula I wherein one or more $Y_1$, $Y_2$, $Y_3$ and $Y_4$ are alkyl of 1 to 9 carbon atoms have excellent solubility in common and inexpensive organic solvents, such as ordorless mineral spirits, kerosene, vegetable oils and the like thereby avoiding the need for more expensive and specialized solvents such as polyhalogenated or alkylated biphenyls which have ordinarily been used to prepare microencapsulated solutions of the color formers of the prior art.

The compounds of this invention may be incorporated in any of the commercially accepted systems known in the carbonless duplicating art. A typical technique for such application is as follows: solutions containing one or more colorless precursor compounds of Formula I optionally in admixture with other color formers in suitable solvents are microencapsulated by well-known procedures, for example, as described in U.S. Pat. No. 3,649,649. The microcapsules are coated on the reverse side of a transfer sheet with the aid of a suitable binder and the coated transfer sheet is then assembled in a manifold with the microcapsule-coated side in contact with a receiving sheet coated with an electronic accepting substance, for example, silton clay or a phenolic resin. Application of pressure to the manifold such as that exerted by a stylus, typewriter or other form of writing or printing causes the capsules on the reverse side to rupture. The solution of the color former released from the ruptured microcapsules flows to the receiving sheet and on contact with the acidic medium thereon forms a yellow to black image of good tinctorial strength and of superior light stability. It is, of course, obvious that variants of this mode of application can be utilized. For example, the receiving sheet in a manifold can alternatively be coated with the subject compounds and the acidic developing agent can be contained in microcapsules applied on the reverse side of the top sheet in the manifold; or the receiving sheet can be coated with a mixture containing both the acidic developing agent and the microencapsulated color former.

It has also been found that when the compounds of Formula I are intimately mixed with an acidic developer of the type generally employed in thermal papers such as described in U.S. Pat. No. 3,539,375, that is, papers which produce a colored image when contacted with a heated stylus or heated type, for example bisphenol A, heating of the mixture produces a colored image of varying shades from yellow to purple depending on the particular compound of the invention employed. The ability of the compounds of Formula I to form a deep color when heated in admixture with an acidic developer such as bisphenol A makes them useful in thermal paper marking systems either where an original or duplicate copy is prepared by contacting the thermal paper with a heated stylus or heated type in any of the methods generally known in the art.

The molecular structure of the compounds of this invention were assigned on the basis of the modes of synthesis, elemental analysis and study of their infrared, nuclear magnetic resonance and mass spectra. The identity and relative abundance of individual isomers in mixtures of Z—CO-pyridinecarboxylic acids and furopyridinones were determined on the basis of thin layer chromatography and nuclear magnetic resonance spectroscopy using the shift reagent tris(dipivalomethanato)europium (III) [Eu(DPM)$_3$].

The following examples will further illustrate the invention without, however, limiting it thereto.

EXAMPLE 1

A. To a mixture containing 10 g. of 2,3-pyridinedicarboxylic anhydride and 26 g. of N,N-diethyl-m-phenetidine in 100 ml. of benzene was added 27 g. of aluminum chloride. After stirring at about 40° C. for 20 hours the reaction mixture was filtered and the solid obtained was added to 800 ml. of ice-water. The resulting precipitate was collected, washed with water and then dissolved in 600 ml. of 10% aqueous sodium hydroxide. After filtering to remove a small amount of insoluble material, the basic aqueous solution was acidified with dilute hydrochloric acid to pH 6. The resulting precipitate was collected, washed with water and dried to give 13.4 g. of product. The filtrate was set aside for further work-up as described in part B hereinbelow. The 13.4 g. of solid material was again dissolved in aqueous base. The resulting solution was filtered and the filtrate adjusted to pH 6 with dilute hydrochloric acid. The pale yellow solid which precipitated was collected, washed with water and dried. The dried material was then slurried in a mixture of 100 ml. of toluene and 10 ml. of ethanol and the pale yellow solid was collected and dried to give 2.6 g. of 3-[4-(diethylamino)-2-ethoxybenzoyl]-2-pyridinecarboxylic acid, m.p. 264°–270° C. (dec.)

B. The filtrate which had been set aside was further acidified to pH 2. The resulting light yellow precipitate was collected, washed with water and dried to give 6.0 g. of product. Recrystallization from ethanol-toluene afforded 4.0 g. of 2-[4-(diethylamino)-2-ethoxybenzoyl]-3-pyridinecarboxylic acid, m.p. 209°–210° C.

C. A mixture containing 1.7 g. of 2-[4-diethylamino)-2-ethoxybenzoyl]-3-pyridinecarboxylic acid, 1.0 g. of diphenylamine, 0.5 g. of urea and 20 ml. of acetic anhydride was stirred 20 hours at room temperature. Almost immediately after the reactants had been combined, the mixture became deep red in color indicating a rapid reaction. The reaction mixture was poured into 300 ml. of toluene and 200 ml. of 5% aqueous ammonium hydroxide. The toluene layer was separated, washed successively with water and saturated aqueous sodium chloride and then passed through a short column of silica gel. The desired product was eluted from the silica gel column with acetone. Evaporation of the acetone under vacuum and crystallization of the residue from 2-propanol-hexane afforded 1.7 g. of 7-[4-(diethylamino)-2-ethoxyphenyl]-7-(diphenylamino)-furo[3,4-b]pyridine-5(7H)-one as a light tan solid, m.p. 183°–185° C. This product produced a red image on acid clay and phenolic resin.

D. Following a procedure similar to that described in part C above, but employing 2.5 g. of 3-[4-(diethylamino)-2-ethoxybenzoyl]-2-pyridinecarboxylic acid, 1.5 g. of diphenylamine, 0.5 g. of urea and 30 ml. of acetic anhydride and allowing the reaction mixture to stir at room temperature for 2 days (the lack of a color change in the reaction mixture after 5 hours indicated a slow reaction), there was obtained 0.2 g. of 5-[4-(diethylamino)-2-ethoxyphenyl]-5-(diphenylamino)furo[3,4-b]-pyridine-7(5H)-one as a brown, gummy material. This product produced a red image on acidic clay and phenolic resin.

EXAMPLE 2

Following a procedure similar to that described in Example 1C hereinabove, but employing 1.7 g. of 2-[4-(diethylamino)-2-ethoxybenzoyl]-3-pyridinecarboxylic acid, 1.1 g. of 3-chloro-N-phenylaniline, 0.5 g. of urea and 20 ml. of acetic anhydride, there was obtained 1.0 g. of 7-[(3-chlorophenyl)phenylamino]-7-[4-(diethylamino)-2-ethoxyphenyl]furo[3,4-b]pyridine-5(7H)-one as a light tan solid, m.p. 130°–131° C. This product produced a red image on acidic clay and phenolic resin.

EXAMPLE 3

A mixture containing 2.0 g. of an isomer mixture comprising 3-[4-(diethylamino)-2-methylbenzoyl]-2-pyridinecarboxylic acid and 2-[4-(diethylamino)-2-methylbenzoyl]-3-pyridinecarboxylic acid, 0.81 g. of 4,4'-bis(dimethylamino)diphenylamine, 6 ml. of acetic anhydride and 0.5 ml. of pyridine was stirred 1 hour at room temperature and then poured into 200 ml. of 5% aqueous ammonium hydroxide and 100 ml. of toluene. The toluene layer was separated, washed with water and saturated aqueous sodium chloride and evaporated to dryness under vacuum. The residue was slurried in a minimum amount of acetone to give 0.5 g. of an isomer mixture comprising 7-[4-(diethylamino)-2-methylphenyl]-7-{bis[4-(dimethylamino)phenyl]amino}-furo[3,4-b]pyridine-5(7H)-one and 5-[4-(diethylamino)-2-methylphenyl]5-{bis[4-(dimethylamino)phenyl]amino}furo[3,4-b]pyridine-7(5H)-one, as a light green solid, m.p. 184°–186° C. A chloroform solution of the product contacted with acidic clay or phenolic resin developed a black image.

EXAMPLE 4

A mixture containing 3.2 g. of an isomer mixture comprising 2-[4-(diethylamino)-2-methylbenzoyl]-3-pyridinecarboxylic acid and 3-[4-(diethylamino)-2-methylbenzoyl]-2-pyridinecarboxylic acid, 2.05 g. of 4,4'-dioctyldiphenylamine, 6 ml. of acetic anhydride and 1.1 ml. of pyridine was stirred 45 minutes at room temperature. After diluting the reaction mixture with 6 ml. of 2-propanol and 3 ml. of hexane, the product was collected, washed with 2-propanol and dried to give 1.5 g. of an isomer mixture comprising 7-[4-(diethylamino)-2-methylphenyl]-7-[bis-(4-octylphenyl)amino]furo[3,4-b]pyridine-5(7H)-one and 5-[4-(diethylamino)-2-methylphenyl]-5-[bis(4-octylphenyl)amino]furo-[3,4-b]pyridine-7(5H)-one as a light purple solid, m.p. 194°–195° C. (dec.)

The filtrate was poured into 5% aqueous ammonium hydroxide and the product was extracted with toluene. The organic extracts were washed with water and saturated aqueous sodium chloride and evaporated to dryness under vacuum. Crystallization of the residue from 2-propanol afforded 1.0 g. of additional product as a white solid. A toluene solution of the product contacted with acidic clay or phenolic resin developed a reddish-purple image.

B. To a mixture containing 1.4 g. of an isomer mixture comprising 2-[4-(diethylamino)-2-methylbenzoyl]-3-pyridinecarboxylic acid and 3-[4-(diethylamino)-2-methylbenzoyl]-2-pyridinecarboxylic acid, 1.0 ml. of thionyl chloride and 60 ml. of N,N-dimethylformamide was added a solution containing 1.84 g. of 4,4'-dioctyldiphenylamine and 0.5 ml. of pyridine in 40 ml. of N,N-dimethylformamide at room temperature. After stirring for one hour, the reaction mixture was poured into 5% aqueous ammonium hydroxide. The precipitate was collected, washed with water and air-dried. The solid was then slurried in a mixture of 30 ml. of hexane and 10 ml. of 2-propanol and filtered to give 1.03 g. of product essentially identical to the product of part A above.

C. A mixture containing 3.13 g. of an isomer mixture comprising 2-[4-(diethylamino)-2-methylbenzoyl]-3-pyridinecarboxylic acid and 3-[4-(diethylamino)-2-methylbenzoyl]-2-pyridinecarboxylic acid, 3.94 g. of 4,4'-dioctyldiphenylamine, 6 ml. of acetic anhydride, 6 ml. of acetic acid and 0.75 g. of urea was stirred 2 hours at room temperature, then poured into 5% aqueous ammonium hydroxide and extracted with toluene. The organic extract was washed with water and saturated aqueous sodium chloride and evaporated to dryness. The residue was analyzed by thin layer chromatography and infrared spectroscopy and shown to contain the desired product identical to the product of part A above.

D. The reaction of part C above was carried out in the absence of urea. The reaction mixture was poured into 5% aqueous ammonium hydroxide and extracted with toluene. The toluene extract was washed with water, saturated aqueous sodium chloride and evaporated to dryness. The residue was analyzed by thin layer chromatography and infrared spectroscopy and shown to contain the desired product identical to the product of part A above.

EXAMPLE 5

Following a procedure similar to that described in Example 4A but employing 1.6 g. of an isomer mixture comprising 2-[4-(diethylamino)-2-methylbenzoyl]-3-pyridinecarboxylic acid and 3-[4-(diethylamino)-2-methylbenzoyl]-2-pyridinecarboxylic acid, 0.6 g. of 4-isopropoxy-N-phenylaniline, 0.5 ml. of pyridine and 6 ml. of acetic anhydride there was obtained 0.7 g. of an isomer mixture comprising 7-[4-(diethylamino)-2-methylphenyl]-7-[4-isopropoxyphenyl)phenylamino]-furo[3,4-b]pyridine-5(7H)-one and 5-[4-(diethylamino)-2-methylphenyl]-5-[(4-isopropoxyphenyl)-phenylamino]furo[3,4-b]pyridine-7(5H)-one as a white solid, m.p. 180°–181° C. A toluene solution of the product contacted with acidic clay or phenolic resin developed a reddish-purple image.

EXAMPLE 6

Following a procedure similar to that described in Example 4A but employing 1.55 g. of an isomer mixture comprising 2-[4-(diethylamino)benzoyl]-3-pyridinecarboxylic acid and 3-[4-(diethylamino)benzoyl]-2-pyridinecarboxylic acid, 1.2 g. of 4-isopropoxy-N-phenylaniline, 0.5 ml. of pyridine and 6 ml. of acetic anhydride there was obtained 0.7 g. of an isomer mixture comprising 7-[4-(diethylamino)phenyl]-7-[(4-isopropoxyphenyl)phenylamino]furo[3,4-b]pyridine-5(7H)-one and 5-[4-(diethylamino)phenyl]-5-[(4-isopropoxyphenyl)phenylamino]furo-[3,4-b]pyridine-7(5H)-one as white solid, m.p. 173°–175° C. A toluene solution of the product contacted with acidic clay or phenolic resin developed an orange image.

EXAMPLE 7

Following a procedure similar to that described in Example 3 but employing 1.55 g. of an isomer mixture comprising 2-[4-(diethylamino)benzoyl]-3-pyridinecarboxylic acid and 3-[4-(diethylamino)benzoyl]-2-pyridinecarboxylic acid, 1.33 g. of 4,4'-bis-(dimethylamino)diphenylamine, 0.5 ml. of pyridine and 6 ml. of acetic anhydride there was obtained 0.83 g. of an isomer mixture comprising 7-[4-(diethylamino)phenyl]-7-{bis[4-(dimethylamino)phenyl]amino}furo[3,4-b]pyridine-5(7H)-one and 5-[4-diethylamino)phenyl]-5-{bis[4-(dimethylamino)phenyl]amino}furo[3,4-b]-7(5H)-one as a light gray-brown solid, m.p. 187° C. (dec.) A toluene solution of the product contacted with acidic clay or phenolic resin developed a dark-brown image.

EXAMPLE 8

A mixture containing 0.2 g. of an isomer mixture comprising 2-[4-(diethylamino)benzoyl]-3-pyridinecarboxylic acid and 3-[4-(diethylamino)benzoyl]-2-pyridinecarboxylic acid, 0.15 g. of diphenylamine and 5 ml. of acetic anhydride was stirred 3 hours at room temperature. The reaction mixture was poured into 100 ml. of toluene and 100 ml. of 5% aqueous ammonium hydroxide. The toluene layer was separated, washed successively with water and saturated aqueous sodium chloride and evaporated to dryness under vacuum. Crystallization of the residue from hexane afforded 0.1 g. of an isomer mixture comprising 7-[4-(diethylamino)phenyl]-7-(diphenylamino)furo[3,4-b]pyridine-5(7H)-one and 5-[4-(diethylamino)phenyl]-5-(diphenylamino)furo[3,4-b]pyridine-7(5H)-one as a tan solid, m.p. 168°–169° C. This product produced a deep orange image on acidic clay and phenolic resin.

EXAMPLE 9

A mixture containing 2.7 g. of an isomer mixture comprising 2-[4-(dimethylamino)benzoyl]-3-pyridinecarboxylic acid and 3-[4-(dimethylamino)benzoyl]-2-pyridinecarboxylic acid and 25 ml. of acetic anhydride was heated to 50° C. After a solution formed, 1.7 g. of diphenylamine was added. The mixture was stirred 2.5 hours at 25° C., 50° C. for 1.5 hours and then cooled to 5° C. The resulting solid was filtered and washed with isopropanol to give 1.3 g. of an isomer mixture comprising 7-[4-(dimethylamino)phenyl]-7-(diphenylamino)furo[3,4-b]pyridine-5(7H)-one and 5-[4-(dimethylamino)phenyl]-5-(diphenylamino)-furo[3,4-b]pyridine-7(5H)-one as a very light orange solid, m.p. 175°–179° C. A toluene solution of the product contacted with acidic clay or phenolic resin developed an orange image.

EXAMPLE 10

Following a procedure similar to that described in Example 9 but employing 2.7 g. of an isomer mixture comprising 2-[4-(dimethylamino)benzoyl]-3-pyridinecarboxylic acid and 3-[4-(dimethylamino)benzoyl]-2-pyridinecarboxylic acid, 4.0 g. of 4,4'-dioctyldiphenylamine and 25 ml. of acetic anhydride there was obtained 2.7 g. of an isomer mixture comprising 7-[4-(dimethylamino)phenyl]-7-[bis(4-octylphenyl)amino]-furo[3,4-b]-pyridine-5(7H)-one and 5-[4-(dimethylamino)phenyl]-5-[bis(4-octylphenyl)amino]-furo[3,4-b]pyridine-7(5H)-one as a light peach solid, m.p. 203°-208° C. A toluene solution of the product contacted with acidic clay or phenolic resin developed an orange image.

EXAMPLE 11

Following a procedure similar to that described in Example 3 but employing 1.6 g. of an isomer mixture comprising 3-[4-(diethylamino)-2-methylbenzoyl]-4-pyridinecarboxylic acid and 4-[4-(diethylamino)-2-methylbenzoyl]-3-pyridinecarboxylic acid, 1.3 g. of 4,4'-bis(dimethylamino)diphenylamine and 6 ml. of acetic anhydride there was obtained 1.5 g. of 3-[4-(diethylamino)-2-methylphenyl]-3-{bis[4-(dimethylamino)phenyl]amino}-furo[3,4-c]pyridine-1(3H)-one and 1-[4-(dimethylamino)-2-methylphenyl]-1-{bis[4-(dimethylamino)phenyl]amino}furo[3,4-c]pyridine-3(1H)-one as a semi-solid. A toluene solution of the product contacted with acidic clay or phenolic resin developed a black image.

EXAMPLE 12

Following a procedure similar to that described in Example 3 but employing 1.6 g. of an isomer mixture comprising 3-[4-(diethylamino)-2-methylbenzoyl]-4-pyridinecarboxylic acid and 4-[4-(diethylamino)-2-methylbenzoyl]-3-pyridinecarboxylic acid, 0.9 g. of diphenylamine and 6 ml. of acetic anhydride there was obtained as isomer mixture comprising 3-[4-(diethylamino)-2-methylphenyl]-3-(diphenylamino)-furo[3,4-c]pyridine-1(3H)-one and 1-[4-(diethylamino)-2-methylphenyl]-1-(diphenylamino)furo[3,4-c]pyridine-3(1H)-one. A toluene solution of the product contacted with acidic clay or phenolic resin developed a red-grape image.

EXAMPLE 13

Following a procedure similar to that described in Example 3 but employing 1.55 g. of an isomer mixture comprising 3-[4-(diethylamino)benzoyl]-4-pyridinecarboxylic acid and 4-[4-(diethylamino)benzoyl]-3-pyridinecarboxylic acid, 1.3 g. of 4,4'-bis-(dimethylamino)diphenylamine, 0.5 ml. of pyridine and 6 ml. of acetic anhydride there was obtained 1.5 g. of an isomer mixture comprising 3-[4-(diethylamino)phenyl]-3-{bis[4-(dimethylamino)phenyl]amino}furo[3,4-c]pyridine-1(3H)-one and 1-[4-(dimethylamino)phenyl]-1-{bis[4-(dimethylamino)phenyl]amino}furo[3,4-c]pyridine-3(1H)-one as a viscous oil. A toluene solution of the product contacted with acidic clay or phenolic resin developed a brown image.

EXAMPLE 14

Following a procedure similar to that described in Example 3 but employing 1.55 g. of an isomer mixture comprising 3-[4-(diethylamino)benzoyl]-4-pyridinecarboxylic acid and 4-[4-(diethylamino)benzoyl]-3-pyridinecarboxylic acid, 1.2 g. of 4-acetamido-N-phenylaniline, 0.5 ml. of pyridine and 6 ml. of acetic anhydride there was obtained 1.5 g. of an isomer mixture comprising 3-[4-(diethylamino)phenyl]-3-[(4-acetamidophenyl)phenylamino]furo[3,4-c]pyridine-1(3H)-one and 1-[4-(diethylamino)phenyl]-1-[(4-acetamidophenyl)phenylamino]furo[3,4-c]pyridine-3(1H)-one as a red-brown solid, m.p. 102°-116° C. A toluene solution of the product contacted with acidic clay or phenolic resin developed an orange-red image.

EXAMPLE 15

3.0 Grams of an isomer mixture comprising 3-[4-(diethylamino)benzoyl]-4-pyridinecarboxylic acid and 4-[4-(diethylamino)benzoyl]-3-pyridinecarboxylic acid in 30 ml. of acetic anhydride was heated to 40° C. After a solution formed, 4.0 g. of 4,4'-dioctyldiphenylamine was added, the mixture was stirred 7 hours, and then allowed to stand another 40 hours. The resulting solution was poured into 100 ml. of ice-water containing 76 ml. of concentrated ammonium hydroxide. The product was extracted into 75 ml. of toluene which was separated, dried over anhydrous calcium chloride and evaporated leaving an oil. Crystallization from hexane yielded 2.8 g. of an isomer mixture comprising 3-[4-(diethylamino)phenyl]-3-[bis(4-octylphenyl)amino]-furo[3,4-c]pyridine-1(3H)-one and 1-[4-(diethylamino)phenyl]-1-[bis(4-octylphenyl)amino]furo[3,4-c]pyridine-3(1H)-one as a tan solid, m.p. 114°-117° C. A toluene solution of the product contacted with acidic clay or phenolic resin developed an orange image.

EXAMPLE 16

Following a procedure similar to that described in Example 3 but employing 3.0 g. of an isomer mixture comprising 3-[4-(diethylamino)benzoyl]-4-pyridinecarboxylic acid and 4-[4-(diethylamino)benzoyl]-3-pyridinecarboxylic acid, 1.7 g. of diphenylamine and 30 ml. of acetic anhydride there was obtained 1.4 g. of an isomer mixture comprising 3-[4-(diethylamino)-phenyl]-3-(diphenylamino)furo[3,4-c]pyridine-1(3H)-one and 1-[4-(diethylamino)phenyl]-1-(diphenylamino)furo[3,4-c]pyridine-3(1H)-one as a light orange solid, m.p. 135°-141° C. A toluene solution of the product contacted with acidic clay or phenolic resin developed an orange image.

EXAMPLE 17

2.6 Grams of an isomer mixture comprising 3-[4-(diethylamino)-2-methylbenzoyl]-4-pyridinecarboxylic acid and 4-[4-(diethylamino)-2-methylbenzoyl]-3-pyridinecarboxylic acid in 30 ml. of acetic anhydride was heated to 40° C. and then 4.0 g. of 4,4'-dioctyldiphenylamine was added. The mixture was stirred for 3 hours at room temperature then poured into 100 ml. of ice-water and 76 ml. of concentrated ammonium hydroxide to yield 5.7 g. of an isomer mixture comprising 3-[4-(diethylamino)-2-methylphenyl]-3-[bis(4-octylphenyl)amino]furo[3,4-c]pyridine-1(3H)-one and 1-[4-(diethylamino)-2-methylphenyl]-1-[bis(4-octylphenyl)amino]furo[3,4-c]pyridine-3(1H)-one as a red solid, m.p. 58°-105° C. A toluene solution of the product contacted with acidic clay or phenolic resin developed a violet image.

EXAMPLE 18

Following a procedure similar to that described in Example 3 but employing 1.63 g. of 3-[4-(diethylamino)-2-methylbenzoyl]-2-pyrazinecarboxylic acid, 1.3 g. of 4,4'-bis-(dimethylamino)diphenylamine, 0.5 ml. of pyridine and 6 ml. of acetic anhydride there was obtained 0.9 g. of 7-[4-(diethylamino)-2-methylphenyl]-7-{bis[4-(dimethylamino)phenyl]amino}furo[3,4-c]pyrazine-5(7H)-one as a light orange solid, m.p. 193.5°-195° C. (dec.) A toluene solution of the product contacted with acidic clay or phenolic resin developed a black image.

EXAMPLE 19

Following a procedure similar to that described in Example 3 but employing 1.6 g. of 3-[4-(diethylamino)-2-methylbenzoyl]-2-pyrazinecarboxylic acid, 0.9 g. of diphenylamine, 0.5 ml. of pyridine and 6 ml. of acetic anhydride there was obtained 0.1 g. of 7-[4-(diethylamino)-2-methylphenyl]-7-(diphenylamino)-furo[3,4-c]pyrazine-5(7H)-one, m.p. 189.5°–191° C. (dec.) A toluene solution of the product contacted with acidic clay or phenolic resin developed a red-grape image.

EXAMPLE 20

Following a procedure similar to that described in Example 3 but employing 0.43 g. of 3-[4-(diethylamino)-benzoyl]-2-pyrazinecarboxylic acid, 0.34 g. of 4,4'-bis-(dimethylamino)-diphenylamine, 0.5 ml. of pyridine and 6 ml. of acetic anhydride there was obtained 0.59 g. of 7-[4-(diethylamino)phenyl]-7-bis[4-(dimethylamino)-phenyl]amino furo[3,4-b]pyrazine-5(7H)-one, m.p. 61°–74° C. A toluene solution of the product contacted with acidic clay or phenolic resin developed a red-brown image.

EXAMPLE 21

Following a procedure similar to that described in Example 3 but employing 0.5 g. of 3-[4-(diethylamino)-benzoyl]-2-pyrazinecarboxylic acid, 0.38 g. of 4-isopropoxy-N-phenylaniline, 0.5 ml. of pyridine and 6 ml. of acetic anhydride there was obtained 0.6 g. of 7-[4-(diethylamino)phenyl]-7-[(4-isopropoxyphenyl)-phenylamino]furo[3,4-b]pyrazine-5(7H)-one, m.p. 75°–82° C. A toluene solution of the product contacted with acidic clay or phenolic resin developed an orange-brown image.

EXAMPLE 22

A mixture containing 0.7 g. of 3-[4-(dimethylamino)-benzoyl]-2-pyrazinecarboxylic acid, 1.0 g. of 4,4'-dioctyldiphenylamine and 7 ml. of acetic anhydride was stirred and gently heated in a warm bath for one hour. The product, 7-[4-(dimethylamino)phenyl]-7-[bis(4-octylphenyl)amino]furo[3,4-b]pyrazine-5(7H)-one was isolated by column chromatography as a rust-colored solid, m.p. 158°–168° C. A toluene solution of the product contacted with acidic clay or phenolic resin developed a reddish-brown image.

EXAMPLE 23

A mixture of 0.1 g. of 3-[4-(diethylamino)benzoyl]-2-pyrazinecarboxylic acid, 0.1 g. of diphenylamine and 2 ml. of acetic anhydride was warmed for several hours and then allowed to stand for three days. The product, 7-[4-(diethylamino)phenyl]-7-(diphenylamino)furo[3,4-b]pyrazine-5(7H)-one was isolated by column chromatography as a light orange solid, m.p. 140°–142.6° C. A toluene solution of this product contacted with acidic clay or phenolic resin developed a red image.

EXAMPLE 24

A mixture containing 0.15 g. of 3-[4-(diethylamino)-benzoyl]-2-pyrazinecarboxylic acid, 0.18 g. of 4,4'-dioctyldiphenylamine and 3 ml. of acetic anhydride was gently heated for 5 hours and then allowed to stand overnight. The product, 7-[4-(diethylamino)phenyl]-7-[bis(4-octylphenyl)amino]furo[3,4-b]pyrazine-5(7H)-one was isolated by column chromatography followed by crystallization from hexane to give a peach solid, m.p. 180°–181° C. A toluene solution of this product contacted with acidic clay or phenolic resin developed a red image.

EXAMPLE 25

A mixture containing 3.1 g. of 3-[4-(diethylamino)-2-methylbenzoyl]-2-pyrazinecarboxylic acid, 3.1 g. of 4,4'-dioctyldiphenylamine and 25 ml. of acetic anhydride was stirred in a warm water bath for 3 hours. The reaction mixture was poured into water and the resulting solid was collected and recrystallized from hexane to give 7-[4-(diethylamino)-2-methylphenyl]-7-[bis(4-octylphenyl)amino]furo[3,4-b]pyrazine-5(7H)-one as a light tan solid, m.p. 180°–187° C. A toluene solution of this product contacted with acidic clay or phenolic resin developed a violet image.

EXAMPLE 26

Following a procedure similar to that described in Example 3 but employing 4.5 g. of an isomer mixture comprising 2-[(1-ethyl-2-methyl-3-indolyl)carbonyl]-3-pyridinecarboxylic acid and 3-[(1-ethyl-2-methyl-3-indolyl)carbonyl]-2-pyridinecarboxylic acid, 3.6 g. of 4-ethoxy-N-phenylaniline, 1 ml. of pyridine and 8 ml. of acetic anhydride there was obtained 5.5 g. of 7-(1-ethyl-2-methyl-3-indolyl)-7-[(4-ethoxyphenyl)phenylamino]-furo[3,4-b]pyridine-5(7H)-one as a tan solid, m.p. 122°–129° C. (dec.) A toluene solution of the product contacted with acidic clay or phenolic resin developed an orange image.

EXAMPLE 27

Following a procedure similar to that described in Example 3 but employing 1.6 g. of an isomer mixture comprising 2-[(1-ethyl-2-methyl-3-indolyl)carbonyl]-3-pyridinecarboxylic acid and 3-[(1-ethyl-2-methyl-3-indolyl)carbonyl]-2-pyridinecarboxylic acid, 2.0 g. of 4,4'-dioctyldiphenylamine, 0.5 ml. of pyridine and 6 ml. of acetic anhydride there was obtained 0.9 g. of 7-(1-ethyl-2-methyl-3-indolyl)-7-[bis(4-octylphenyl)amino]-furo[3,4-b]pyridine-5(7H)-one as a light tan solid, m.p. 187° C. (dec.) A toluene solution of the product contacted with acidic clay or phenolic resin developed an orange image.

EXAMPLE 28

Following a procedure similar to that described in Example 3 but employing 1.6 g. of an isomer mixture comprising 2-[(1-ethyl-2-methyl-3-indolyl)carbonyl]-3-pyridinecarboxylic acid, and 3-[(1-ethyl-2-methyl-3-indolyl)carbonyl]-2-pyridinecarboxylic acid, 1.1 g. of 4-(dimethylamino)-N-phenylaniline, 0.5 ml. of pyridine and 6 ml. of acetic anhydride there was obtained 1.3 g. of 7-(1-ethyl-2-methyl-3-indolyl)-7-{[4-(dimethylamino)phenyl]phenylamino}furo[3,4-b]pyridine-5(7H)-one as a gray solid, m.p. 191°–192° C. (dec.) A chloroform solution of the product contacted with acidic clay or phenolic resin developed a brown image.

EXAMPLE 29

Following a procedure similar to that described in Example 3 but employing 1.6 g. of an isomer mixture comprising 2-[(1-ethyl-2-methyl-3-indolyl)carbonyl]-3-pyridinecarboxylic acid and 3-[(1-ethyl-2-methyl-3-indolyl)carbonyl]-2-pyridinecarboxylic acid, 1.3 g. of 4,4'-bis-(dimethylamino)diphenylamine, 0.5 ml. of pyridine and 6 ml. of acetic anhydride there was obtained 0.35 g. of 7-(1-ethyl-2-methyl-3-indolyl)-7-{bis[4-(dimethylamino)phenyl]amino}furo[3,4-b]pyridine-5(7H)-one as a white solid, m.p. 205°–206° C. (dec.) A chloroform solution of the product contacted with acidic clay or phenolic resin developed a brown image.

EXAMPLE 30

Following a procedure similar to that described in Example 3 but employing 1.6 g. of an isomer mixture comprising 2-[(1-ethyl-2-methyl-3-indolyl)carbonyl]-3-pyridinecarboxylic acid and 3-[(1-ethyl-2-methyl-3-indolyl)carbonyl]-2-pyridinecarboxylic acid, 0.95 g. of N-phenyl-m-toluidine, 0.5 ml. of pyridine and 6 ml. of acetic anhydride there was obtained 7-(1-ethyl-2-methyl-3-indolyl)-7-(m-tolylphenylamino)furo[3,4-b]pyridine-5(7H)-one as a yellow solid, m.p. 178°–190° C. (dec.) A toluene solution of the product contacted with acidic clay or phenolic resin developed an orange image.

EXAMPLE 31

A mixture containing 4.5 g. of an isomer mixture comprising 2-[(1-ethyl-2-methyl-3-indolyl)carbonyl]-3-pyridinecarboxylic acid and 3-[(1-ethyl-2-methyl-3-indolyl)carbonyl]-2-pyridinecarboxylic acid, 2.5 g. of diphenylamine and 30 ml. of acetic anhydride was stirred 6.5 hours, then treated with one ml. of pyridine and allowed to stand overnight. The reaction mixture was poured into 750 ml. of water and the resulting solid product was purified by column chromatography affording 7-(1-ethyl-2-methyl-3-indolyl)-7-(diphenylamino)furo[3,4-b]-pyridine-5(7H)-one as a light orange solid, m.p. 132.5°–136° C. A toluene solution of the product contacted with acidic clay or phenolic resin developed an orange image.

EXAMPLE 32

Following a procedure similar to that described in Example 3 but employing 1.6 g. of an isomer mixture comprising 3-[(1-ethyl-2-methyl-3-indolyl)carbonyl]-4-pyridinecarboxylic acid and 4-[(1-ethyl-2-methyl-3-indolyl)carbonyl]-3-pyridinecarboxylic acid, 0.9 g. of diphenylamine, 0.5 ml. of pyridine and 6 ml. of acetic anhydride there was obtained 1-(1-ethyl-2-methyl-3-indolyl)-1-(diphenylamino)furo[3,4-c]pyridine-3(1H)-one as a viscous oil. A toluene solution of the product contacted with acidic clay or phenolic resin developed an orange image.

EXAMPLE 33

Following a procedure similar to that described in Example 3 but employing 3.1 g. of 3-[(1-ethyl-2-methyl-3-indolyl)carbonyl]-2-pyrazinecarboxylic acid, 2.2 g. of 4-ethoxy-N-phenylaniline, 2 ml. of pyridine and 10 ml. of acetic anhydride there was obtained 1.1 g. of 7-(1-ethyl-2-methyl-3-indolyl)-7-[(4-ethoxyphenyl)-phenylamino]furo[3,4-b]pyrazine-5(7H)-one as a light brown solid, m.p. 120°–135° C. (dec.) A toluene solution of the product contacted with acidic clay or phenolic resin developed a reddish-orange image.

EXAMPLE 34

Following a procedure similar to that described in Example 3 but employing 0.8 g. of 3-[(1-ethyl-2-methyl-3-indolyl)carbonyl]-2-pyrazinecarboxylic acid, 1.0 g. of 4,4'-dioctyldiphenylamine, 0.25 ml. of pyridine and 3 ml. of acetic anhydride there was obtained 7-(1-ethyl-2-methyl-3-indolyl)-7-[bis(4-octylphenyl)amino]furo[3,4-b]pyrazine-5(7H)-one as a semi-solid. A toluene solution of the product contacted with acidic clay or phenolic resin developed an orange image.

EXAMPLE 35

A mixture containing 4 g. of 3-[(1-ethyl-2-methyl-3-indolyl)carbonyl]-2-pyrazinecarboxylic acid, 1.7 g. of diphenylamine and 15 ml. of acetic anhydride was stirred 1 hour at room temperature and then 30 minutes with gentle warming. The product, 7-(1-ethyl-2-methyl-3-indolyl)-7-(diphenylamino)furo[3,4-b]pyrazine-5(7H)-one was isolated by column chromatography as a red solid, m.p. 98°–100° C. A toluene solution of this product contacted with acidic clay or phenolic resin developed an orange image.

It is contemplated that by following procedures similar to those described in the foregoing examples but employing the appropriate Z—CO-pyridinecarboxylic acids of Formula II and appropriately substituted diarylamines of Formula III there will be obtained the compounds of Formula I, Examples 36–65, presented in the following table.

| Ex. | A | $R_3$ | $R_4$ | $R_5$ | $R_6$ |
|---|---|---|---|---|---|
| 36 | (pyridine ring) | $C_2H_5O$ | $C_2H_5$ | $C_2H_5$ | — |
| 37 | " | $(CH_3)_2N$ | $CH_3$ | $CH_3$ | — |
| 38 | " | H | $C_2H_5$ | $C_6H_5CH_2$ | — |
| 39 | " | Cl | $C_2H_5$ | $C_2H_5$ | — |
| 40 | " | — | — | — | H |
| 41 | " | — | — | — | H |

-continued

| | | | | | |
|---|---|---|---|---|---|
| 42 | " | — | — | — | CH₃ |
| 43 | " | — | — | — | n-C₄H₉ |
| 44 | " | — | — | — | n-C₈H₁₇ |
| 45 | (pyridyl) | C₂H₅O | C₂H₅ | C₂H₅ | — |
| 46 | " | (CH₃)₂N | CH₃ | CH₃ | — |
| 47 | " | H | C₂H₅ | C₆H₅CH₂ | — |
| 48 | " | Cl | C₂H₅ | C₂H₅ | — |
| 49 | " | — | — | — | H |
| 50 | " | — | — | — | H |
| 51 | " | — | — | — | CH₃ |
| 52 | " | — | — | — | n-C₄H₉ |
| 53 | " | — | — | — | n-C₈H₁₇ |
| 54 | (pyridyl) | — | — | — | H |
| 55 | " | n-C₄H₉ | CH₃ | CH₃ | — |
| 56 | " | (CH₃)₂CHCH₂O | CH₃ | CH₃ | — |
| 57 | " | (sec-C₄H₉)₂N | sec-C₄H₉ | sec-C₄H₉ | — |
| 58 | (pyridyl) | Br | CH₃ | CH₃ | — |
| 59 | " | — | — | — | n-C₁₈H₃₇ |
| 60 | (pyrazinyl) | — | — | — | (CH₃)₂CH(CH₂)₈ |
| 61 | " | — | — | — | n-C₆H₁₃ |
| 62 | " | — | — | — | C₂H₅ |
| 63 | " | — | — | — | C₂H₅ |
| 64 | " | H | CH₃ | CH₃ | — |
| 65 | " | C₂H₅ | C₂H₅ | C₂H₅ | — |

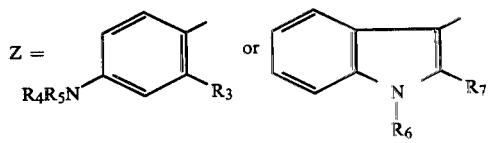

Z =  R₄R₅N—C₆H₃(R₃)—  or  indolyl (N-R₆, 2-R₇)

| Ex. | R₇ | Y₁ | Y₂ | Y₃ | Y₄ |
|---|---|---|---|---|---|
| 36 | — | H | 4-C₈H₁₇ | H | 4-C₈H₁₇ |
| 37 | — | H | 4-C₈H₁₇ | H | 4-arylalkyl* |
| 38 | — | H | H | H | 3-CH₃ |
| 39 | — | H | H | H | 4-NHSO₂C₆H₄CH₃-p |
| 40 | CH₃ | H | H | H | H |
| 41 | C₆H₅ | H | 4-C₈H₁₇ | H | 4-arylalkyl* |
| 42 | CH₃ | H | H | H | 3-Cl |
| 43 | CH₃ | H | H | H | 4-NHSO₂C₆H₅ |
| 44 | CH₃ | H | H | H | H |
| 45 | — | H | 4-C₈H₁₇ | H | 4-C₈H₁₇ |
| 46 | — | H | 4-C₈H₁₇ | H | 4-arylalkyl* |
| 47 | — | H | H | H | 3-CH₃ |
| 48 | — | H | H | H | 4-NHSO₂C₆H₄CH₃-p |
| 49 | CH₃ | H | H | H | H |
| 50 | C₆H₅ | H | 4-C₈H₁₇ | H | 4-arylalkyl* |
| 51 | CH₃ | H | H | H | 3-Cl |
| 52 | CH₃ | H | H | H | 4-NHSO₂C₆H₅ |
| 53 | CH₃ | H | H | H | H |
| 54 | CH₃ | H | H | H | H |
| 55 | — | H | H | H | 4-Br |
| 56 | — | 2-Cl | 4-Cl | 2-Cl | 4-Cl |
| 57 | — | H | H | H | H |
| 58 | — | H | 3-C₄H₉O | H | 3-C₄H₉O |
| 59 | CH₃ | 3-C₂H₅ | 5-C₉H₁₉ | 3-C₂H₅ | 5-C₉H₁₉ |
| 60 | H | H | H | 3-(CH₃)₃C | H |
| 61 | CH₃ | H | H | 4-n-C₆H₁₃ | H |
| 62 | CH₃ | H | H | H | 4-NHCOC₄H₉ |
| 63 | CH₃ | H | H | H | 4-NH₂ |
| 64 | — | H | H | H | 4-CHCH₂C₆H₅ |
| | | | | | \|  |
| | | | | | CH₃ |

| -continued | | | | |
|---|---|---|---|---|
| 65 | — | H | 2-Cl | H | 4-F |

*Derived from octylated arylalkylated diphenylamine sold by the B.F. Goodrich Chemical Co under the trademark Good-rite Antioxidant 3190.

EXAMPLE 66

A solution containing 1.46 g. of the color former of Example 28 in 60 ml. of isopropylbiphenyl and a solution containing 5 g. of carboxymethylcellulose in 200 ml. of water were mixed and emulsified by rapid stirring. The desired particle size (5 microns) was checked by microscope. To the emulsion was added a solution containing 15 g. of pigskin gelatin in 120 ml. of water. The pH was adjusted to 6.5 with 10% aqueous sodium hydroxide with rapid stirring, and following the gradual addition of 670 ml. of water at 50° C. the pH was adjusted to 4.5 with 10% aqueous acetic acid with continued rapid stirring. After 5 minutes the mixture was cooled to 15° C., treated with 10 g. of 25% aqueous glutaraldehyde and rapidly stirred for 15 minutes. The resulting microcapsule dispersion was stirred more slowly overnight, diluted with water to 1120 g. and coated on white typewriter paper sheets (0.0015 in. film thickness). The sheets were air dried. Duplicate typewritten images were made on receiving sheets coated with either phenolic resin or acidic clay. The color former of Example 28 produced a brown image on both types of receiving sheets.

EXAMPLE 67

A polyvinyl alcohol dispersion of the color former of Example 28 was prepared by shaking 1 hour on a paint shaker a mixture containing 2.0 g. of the color former, 3.7 g. of water, 8.6 g. of 10% aqueous polyvinyl alcohol and 10 g. of zirconium grinding beads. A polyvinyl alcohol dispersion of bisphenol A was prepared by shaking a mixture containing 9.8 g. of bisphenol A, 18.2 g. of water, 42 g. of 10% aqueous polyvinyl alcohol and 70 ml. of zirconium grinding beads. The coating mixture was made by combining and thoroughly mixing 2.1 g. of the polyvinyl alcohol dispersion of the color former with 47.9 g. of the polyvinyl alcohol dispersion of bisphenol A. The coating mixture was applied (at thicknesses of 0.003 and 0.0015 inches) to white mimeo paper sheets and the sheets were dried at room temperature. Contacting the coated sheets with a heated stylus at a temperature between 110° C. and 150° C. produced a purple image.

We claim:

1. A compound having the formula:

[structure]

wherein
A is

[structures of A: pyridine isomers]

$Y_1$, $Y_2$, $Y_3$ and $Y_4$ are the same or different and are selected from the group consisting of hydrogen, halo, lower alkoxy, alkyl having from 1 to 9 carbon atoms, phenyl-lower-alkyl and $NR_1R_2$ where $R_1$ is hydrogen or lower alkyl and $R_2$ is hydrogen, lower alkyl, lower alkanoyl, phenylsulfonyl or lower-alkyl-substituted phenylsulfonyl;

Z is

[structures with $R_4R_5N$, $R_3$ or indole with $R_6$, $R_7$]

in which
$R_3$ is hydrogen, lower alkyl, lower alkoxy, halo or di-lower-alkylamino;
$R_4$ is lower alkyl;
$R_5$ is lower-alkyl or benzyl;
$R_6$ is hydrogen or non-tertiary alkyl having from 1 to 18 carbon atoms; and
$R_7$ is hydrogen, phenyl or non-tertiary lower alkyl.

2. A compound according to claim 1 wherein A is

[structures]

3. A compound according to claim 2 wherein A is

[structures]

4. A compound according to claim 3 wherein Z is

[structure with $R_4R_5N$, $R_3$]

5. A compound according to claim 4 wherein $R_3$ is hydrogen or lower-alkyl and $R_4$ and $R_5$ are each lower alkyl.

6. A compound according to claim 5 wherein $Y_1$ and $Y_3$ are each hydrogen.

7. A compound according to claim 6 wherein $Y_2$ and $Y_4$ are the same or different and are selected from the group consisting of hydrogen and alkyl having from 1 to 9 carbon atoms.

8. A compound according to claim 3 wherein Z is

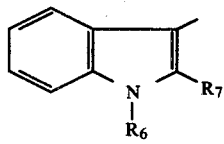

9. A compound according to claim 8 wherein $Y_1$ and $Y_3$ are each hydrogen.

10. A compound according to claim 9 wherein $Y_2$ and $Y_4$ are the same or different and are selected from the group consisting of hydrogen and alkyl having from 1 to 9 carbon atoms.

11. A compound according to claim 2 wherein A is

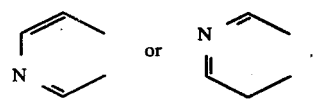

12. A compound according to claim 11 wherein Z is

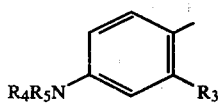

13. A compound according to claim 11 wherein Z is

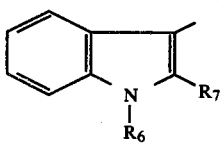

14. A compound according to claim 1 wherein A is

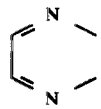

15. A compound according to claim 14 wherein Z is

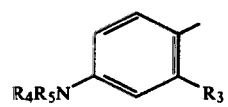

16. A compound according to claim 14 wherein Z is

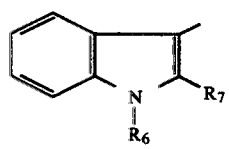

17. 7-[4-(dimethylamino)phenyl]-7-(diphenylamino)-furo[3,4-b]pyridine-5(7H)-one according to claim 7.

18. 5-[4-(dimethylamino)phenyl]-5-(diphenylamino)-furo[3,4-b]pyridine-7(5H)-one according to claim 7.

19. 7-[4-(dimethylamino)phenyl]-7-[bis(4-octylphenyl)amino]furo[3,4-b]pyridine-5(7H)-one according to claim 7.

20. 5-[4-(dimethylamino)phenyl]-5-[bis(4-octylphenyl)amino]furo[3,4-b]pyridine-7(5H)-one according to claim 7.

21. 7-[4-(diethylamino)-2-methylphenyl]-7-[bis(4-octylphenyl)amino]furo[3,4-b]pyridine-5(7H)-one according to claim 7.

22. 5-[4-(diethylamino)-2-methylphenyl]-5-[bis(4-octylphenyl)amino]furo[3,4-b]pyridine-7(5H)-one according to claim 7.

23. 7-(1-ethyl-2-methyl-3-indolyl)-7-(diphenylamino)-furo[3,4-b]pyridine-5(7H)-one according to claim 10.

24. 5-(1-ethyl-2-methyl-3-indolyl)-5-(diphenylamino)-furo[3,4-b]pyridine-7(5H)-one according to claim 10.

25. 7-(1-ethyl-2-methyl-3-indolyl)-7-[bis(4-octylphenyl)amino]furo[3,4-b]pyridine-5(7H)-one according to claim 10.

26. 5-(1-ethyl-2-methyl-3-indolyl)-5-[bis(4-octylphenyl)amino]furo[3,4-b]pyridine-7(5H)-one according to claim 10.

* * * * *

UNITED STATES PATENT AND TRADEMARK OFFICE
CERTIFICATE OF CORRECTION

PATENT NO. : 4,211,872

DATED : July 8, 1980

INVENTOR(S) : Paul J. Schmidt and William M. Hung

It is certified that error appears in the above-identified patent and that said Letters Patent is hereby corrected as shown below:

Column 2, formula between lines 62-66,

" 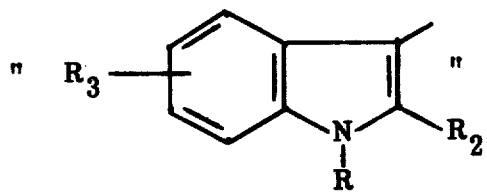 "  should read --  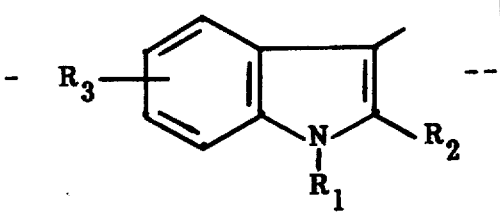 --

Column 26, claim 1, line 15,

" 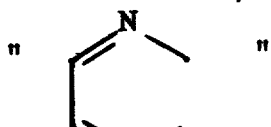 "  should read --  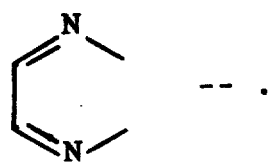 -- .

Column 26, claim 2,

" 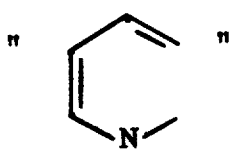 "  should read --  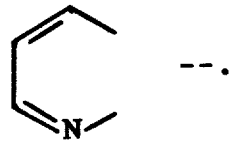 -- .

UNITED STATES PATENT AND TRADEMARK OFFICE
CERTIFICATE OF CORRECTION

PATENT NO. : 4,211,872

DATED : July 8, 1980

INVENTOR(S) : Paul J. Schmidt and William M. Hung

It is certified that error appears in the above-identified patent and that said Letters Patent is hereby corrected as shown below:

Column 27, claim 11,

" 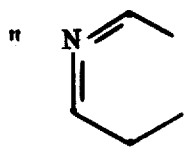 " should read -- 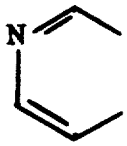 --.

Signed and Sealed this

Twenty-sixth Day of November 1985

[SEAL]

Attest:

DONALD J. QUIGG

Attesting Officer　　Commissioner of Patents and Trademarks